US00PP34337P2

(12) United States Plant Patent
Kientzler

(10) Patent No.: US PP34,337 P2
(45) Date of Patent: Jun. 14, 2022

(54) **NEW GUINEA *IMPATIENS* PLANT NAMED 'KIYONITA'**

(50) Latin Name: *Impatiens hawkeri*
Varietal Denomination: Kiyonita

(71) Applicant: Ludwig Kientzler, Gensingen (DE)

(72) Inventor: Ludwig Kientzler, Gensingen (DE)

(73) Assignee: INNOVAPLANT ZIERPFLANZEN GmbH & Co. KG, Gensingen (DE)

( * ) Notice: Subject to any disclaimer, the term of this patent is extended or adjusted under 35 U.S.C. 154(b) by 0 days.

(21) Appl. No.: 17/512,344

(22) Filed: Oct. 27, 2021

(51) Int. Cl.
*A01H 5/02* (2018.01)
*A01H 6/16* (2018.01)

(52) U.S. Cl.
USPC ..... Plt./318.7

(58) Field of Classification Search
USPC ..... Plt./263.1, 317, 318.1, 318.7
See application file for complete search history.

*Primary Examiner* — Karen M Redden
(74) *Attorney, Agent, or Firm* — C. Anne Whealy

(57) ABSTRACT

A new and distinct cultivar of New Guinea *Impatiens* plant named 'Kiyonita', characterized by its upright to broadly spreading and mounded plant habit; freely branching habit; dense and bushy growth habit; durable and dark green-colored leaves; freely flowering habit; large and rounded bright red-colored flowers; and flowers positioned above and beyond the foliar plane.

1 Drawing Sheet

Figure 1:
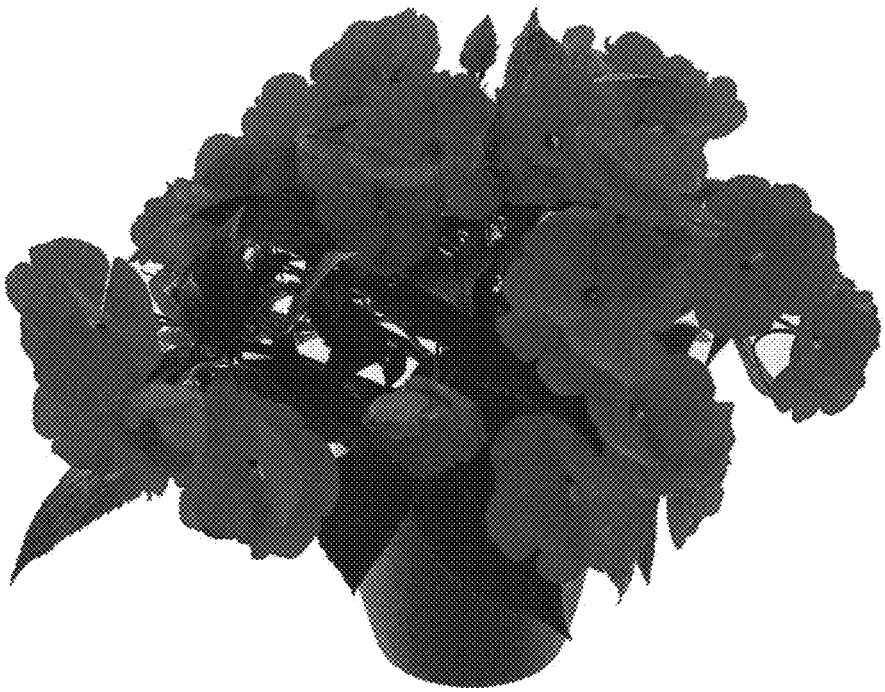

Botanical designation: *Impatiens hawkeri.*
Cultivar denomination: 'KIYONITA'.

STATEMENT REGARDING PRIOR DISCLOSURES BY INVENTOR/APPLICANT & ASSIGNEE

An European Community Plant Breeder's Rights application for the instant plant was filed by the Assignee, Innovaplant Zierpflanzen GmbH & Co. KG of Gensingen, Germany on Sep. 8, 2021, application number 2021/2218. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of New Guinea *Impatiens* plant, botanically known as *Impatiens hawkeri*, and hereinafter referred to by the name 'Kiyonita'.

The new *Impatiens* plant is a product of a planned breeding program conducted by the Inventor in Gensingen, Germany. The objective of the breeding program was to develop new compact and freely branching *Impatiens* plants with numerous flowers and attractive leaf and flower colors.

The new *Impatiens* plant originated from a cross-pollination made by the Inventor in November, 2018 of *Impatiens hawkeri* 'Kiorotina', not patented, as the female, or seed, parent with a proprietary selection of the *Impatiens hawkeri* identified as code number 212-1, not patented, as the male, or pollen, parent. The new *Impatiens* plant was discovered and selected by the Inventor as a flowering plant within the progeny of the stated cross-pollination in a controlled greenhouse environment in Gensingen, Germany in April, 2019.

Asexual reproduction of the new *Impatiens* plant by terminal cuttings propagated in a controlled greenhouse environment in Gensingen, Germany since June, 2019 has shown that the unique features of this new *Impatiens* plant are stable and reproduced true to type in successive generations of asexual reproduction.

SUMMARY OF THE INVENTION

Plants of the new *Impatiens* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Kiyonita'. These characteristics in combination distinguish 'Kiyonita' as a new and distinct *Impatiens* plant:

1. Upright to broadly spreading and mounded plant habit.
2. Freely branching habit; dense and bushy growth habit.
3. Durable and dark green-colored leaves.
4. Freely flowering habit.
5. Large and rounded bright red-colored flowers.
6. Flowers positioned above and beyond the foliar plane.

Plants of the new *Impatiens* differ primarily from plants of the female parent, 'Kiorotina', in the following characteristics:

1. Plants of the new *Impatiens* are more mounding than and not as upright as plants of 'Kiorotina'.
2. Plants of the new *Impatiens* are more freely branching than plants of 'Kiorotina'.

3. Flowers of plants of the new *Impatiens* are more rounded than flowers of plants of 'Kiorotina'.
4. Leaf apices of plants of the new *Impatiens* are more durable and less sensitive to damage due to salt than leaf apices of plants of 'Kiorotina'.

Plants of the new *Impatiens* differ primarily from plants of the male parent selection in plant habit as plants of the new *Impatiens* are more uniform than plants of the male parent selection.

Plants of the new *Impatiens* can be compared to plants of *Impatiens hawkeri* 'Kiorona', disclosed in U.S. Plant Pat. No. 18,822. In side-by-side comparisons, plants of the new *Impatiens* differ primarily from plants of 'Kiorona', in the following characteristics:

1. Plants of the new *Impatiens* are taller than and not as compact as plants of 'Kiorona'.
2. Plants of the new *Impatiens* flower earlier than plants of 'Kiorona'.
3. Flowers of plants of the new *Impatiens* are brighter red in color than flowers of plants of 'Kiorona'.

BRIEF DESCRIPTION OF THE PHOTOGRAPHS

The accompanying photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph at the top of sheet (FIG. 1) is a side perspective view of a typical flowering plant of 'Kiyonita' grown in a container.

Figure 2:
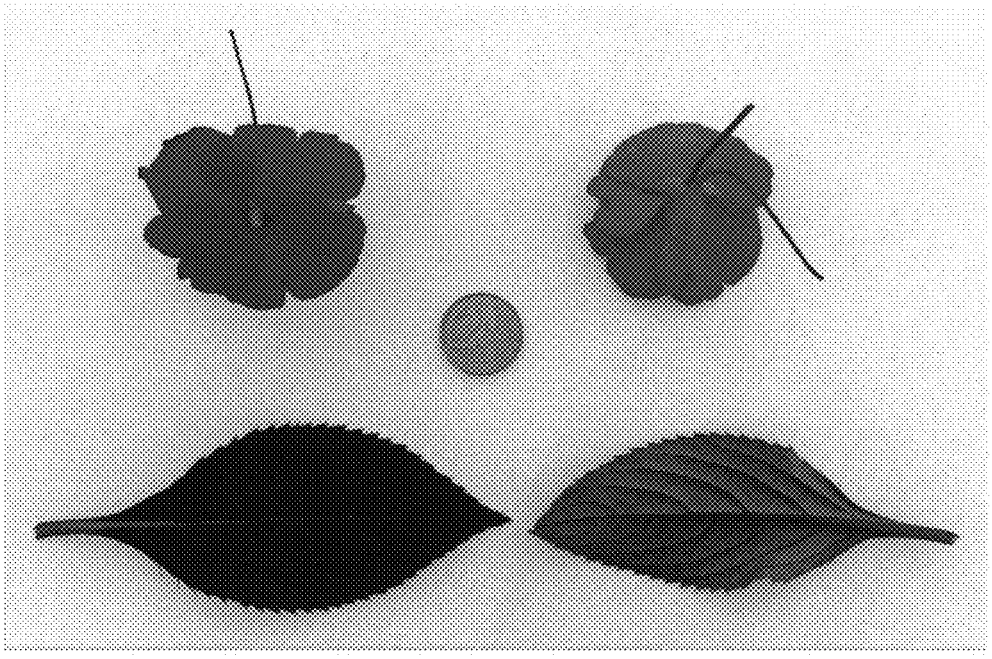

The photograph at the bottom of the sheet (FIG. 2) is a close-up view of the upper surfaces (left) and lower surfaces (right) of typical flowers and leaves of 'Kiyonita'.

DETAILED BOTANICAL DESCRIPTION

The aforementioned photographs and following observations and measurements describe plants grown in Gensingen, Germany during the late spring and early summer in 12-cm containers in a glass-covered greenhouse and under cultural practices typical of commercial New Guinea *Impatiens* production. During the production of the plants, day temperatures ranged from 18° C. to 25° C. and night temperatures ranged from 20° to 22° C. Plants were twelve weeks old when the photographs and detailed description were taken. In the following description, color references are made to The Royal Horticultural Society Colour Chart, 2015 Edition, except where general terms of ordinary dictionary significance are used.

Botanical classification: *Impatiens hawkeri* 'Kiyonita'.

Parentage:

*Female, or seed, parent.*—*Impatiens hawkeri* 'Kiorotina', not patented.

*Male, or pollen parent.*—Proprietary selection of *Impatiens hawkeri* identified as code number 212-1, not patented.

Propagation:

*Type.*—By terminal vegetative cuttings.

*Time to initiate roots, summer.*—About eight to ten days at temperatures about 20° C. to 35° C.

*Time to initiate roots, winter.*—About ten to twelve days at temperatures about 20° C. to 25° C.

*Time to produce a rooted young plant, summer.*—About two to three weeks at temperatures about 20° C. to 35° C.

*Time to produce a rooted young plant, winter.*—About three to four weeks at temperatures about 20° C. to 25° C.

*Root description.*—Fibrous, medium in thickness; typically white to brown in color, actual color of the roots is dependent on substrate composition, water quality, fertilizers, substrate temperature and physiological age of roots.

*Rooting habit.*—Moderately freely branching; medium density.

Plant description:

*Plant and growth habit.*—Upright to broadly spreading and mounded plant habit; moderately vigorous and moderate growth rate.

*Branching habit.*—Freely branching habit; about three primary lateral branches developing at the base each with about four to five secondary branches; dense and bushy growth habit; pinching, that is, removal of the terminal apices, is typically not required.

*Plant height, soil level to top of foliar plane.*—About 18.4 cm.

*Plant height, soil level to top of floral plane.*—About 21 cm.

*Plant diameter or spread.*—About 37.4 cm.

*Lateral branches.*—Length: About 10.1 cm. Diameter: About 6.5 mm. Internode length: About 4.8 cm. Strength: Moderately strong. Aspect: Erect to about 50° from vertical. Texture and luster: Smooth, glabrous; glossy. Color, developing: Close to 187A. Color, developed: Close to 183A to 183B; at the internodes, close to 183B.

Leaf description:

*Arrangement.*—Opposite or in whorls, single.

*Length.*—About 11.4 cm.

*Width.*—About 4.6 cm.

*Shape.*—Elliptic.

*Apex.*—Apiculate to acuminate.

*Base.*—Acuminate.

*Margin.*—Serrate with mucronate tips and ciliation.

*Texture and luster, upper surface.*—Smooth, glabrous; slightly velvety; slightly glossy.

*Texture and luster, lower surface.*—Smooth, glabrous; slightly to moderately glossy.

*Venation pattern.*—Pinnate.

*Color.*—Developing leaves, upper surface: Darker than 143A. Developing leaves, lower surface: Close to 146B. Fully expanded leaves, upper surface: Close to NN137A slightly tinged with close to 147A; mucronate tips at margins, close to 150D, 152B and 182D; venation, close to 183B. Fully expanded leaves, lower surface: Close to 148B; venation, close to 182C.

*Petioles.*—Length: About 2.9 cm. Diameter: About 3 mm by 4 mm. Strength: Moderately strong; flexible. Texture and luster, upper and lower surfaces: Smooth, glabrous; moderately glossy. Color, upper surface: Close to 182B and 183B to 183C. Color, lower surface: Close to 183B to 183C.

Flower description:

*Flower type and flowering habit.*—Large and rounded single axillary flowers; freely flowering habit with usually about 110 flower buds and flowers developing per plant; flowers positioned above and beyond the foliar plane and typically face upright to outwardly.

*Flower longevity*.—Flowers last about one week under greenhouse conditions; petals self-cleaning, gynoecium persistent.

*Fragrance*.—None detected.

*Natural flowering season*.—Year-round under greenhouse conditions; in the garden, flowering from spring until fall in Germany; plants begin flowering about 60 to 70 days after planting young plants.

*Flower diameter*.—About 6.2 cm by 6.4 cm.

*Flower depth*.—About 2.5 cm; with spur, close to 7 cm.

*Flower buds*.—Length: About 1.6 cm. Spur length: About 3.5 cm. Diameter: About 1 cm by 1.2 cm. Shape: Ovoid; spurred. Texture and luster: Smooth, glabrous; moderately glossy. Color: Petals, close to 45A, 53A and 51B to 51C; towards the apex, close to 187A to 187B; spur, close to 45A.

*Petals*.—Quantity and arrangement: Five petals arranged in a single whorl; one banner petal, two lateral petals and two lower petals. Length, banner petal: About 3.3 cm. Length, lateral petals: About 2.7 cm. Length, lower petals: About 3.5 cm. Width, banner petal: About 5.4 cm. Width, lateral petals: About 3.7 cm. Width, lower petals: About 4.5 cm. Shape, banner petal: Reniform. Shape, lateral and lower petals: Broadly obcordate to close to reniform. Apex, all petals: Broadly emarginate. Base, banner petal: Truncate. Base, lateral petals: Broadly cuneate. Base, lower petals: Acute. Margin, all petals: Entire, occasionally with one or two shallow to moderately deep incisions; coarsely undulate. Texture and luster, all petals, upper surface: Smooth, glabrous; velvety; matte. Texture and luster, all petals, lower surface: Smooth, glabrous; slightly velvety; matte. Color: When opening, upper surface: Close to 45B; towards the margins and apex, a blend of 45A and 45B; lower petals proximally, close to 53B. When opening, lower surface: Close to 44A to 44B; towards the base, close to 43B; keel on banner petal, close to N45A; lower petals proximally, close to 53B. Fully opened, upper surface: Close to 45A; lower petals proximally, close to N45A; venation, similar to lamina colors. Fully opened, lower surface: Close to 44B; towards the base, close to 43A to 43B; keel on banner petal, close to 46A to 46B; lower petals proximally, close to N45A; midvein, close to 53A and lateral venation, similar to lamina colors.

*Sepals*.—Quantity and arrangement: Three arranged in a single whorl; one dorsal sepal modified into an elongated spur and two lateral sepals. Length, dorsal sepal (excluding spur): About 1.8 cm. Length, lateral sepals: About 1.2 cm. Width, dorsal sepal: About 1.1 cm. Width, lateral sepals: About 6 mm. Shape, dorsal sepal: Broadly ovate; concave. Shape, lateral sepals: Ovate; concave. Apex, dorsal sepal: Abruptly acute. Apex, lateral sepals: Apiculate. Base, all sepals: Cuneate. Margin: Entire. Texture and luster, upper surface, all sepals: Smooth, glabrous; matte. Texture and luster, lower surface, all sepals: Smooth, glabrous; slightly glossy. Color, dorsal sepal: When opening, upper surface: Close to 45D; towards the base, close to 52B. When opening, lower surface: Close to 54B; towards the apex, close to 51B; midvein, close to 50A. Fully opened, upper surface: Close to 45C; towards the base, close to 53D and basal margins, close to 54D. Fully opened, lower surface: Close to 51C; towards the apex and margins, close to 50A; midvein, close to 47B. Color, lateral sepals: When opening, upper surface: Close to 53C. When opening, lower surface: Close to 47B; towards the base, close to 54B. Fully opened, upper surface: Close to 47B; towards the apex, close to 145C and at the apex, close to 53A. Fully opened, lower surface: Close to 47A; towards the base, close to 51B. Spur length: About 5.3 cm. Spur diameter: At flower, about 1.75 mm; at apex, less than 1 mm. Spur texture and luster: Smooth, glabrous; glossy. Spur color: Close to 46A; towards the apex, close to 187A.

*Peduncles*.—Length: About 5 cm. Diameter: About 1.5 mm. Angle: About 30° from vertical. Strength: Relatively weak. Texture and luster: Smooth, glabrous; glossy. Color, upper and lower surfaces: Close to 53A.

*Reproductive organs*.—Stamens: Quantity: Four. Filament length: About 4 mm. Filament color: Close to 42B. Anther size: About 1 mm by 3 mm. Anther shape: Oblong. Anther color: Close to 159A to 159B. Pollen amount: Abundant. Pollen color: Close to 155B. Pistils: Quantity per flower: One. Pistil length: About 1 mm. Style length: About 0.5 mm. Style color: Close to 47A. Stigma diameter: About 0.8 mm. Stigma shape: Round, flattened. Stigma color: Close to 157A. Ovary color: Close to N144D.

*Seeds and fruit*.—To date, seed nor fruit development has not been observed on plants of the new *Impatiens*.

Pathogen & pest resistance: To date, plants of the new *Impatiens* have not been observed to be resistant to pathogens and pests common to New Guinea *Impatiens* plants.

Temperature tolerance: Plants of the new *Impatiens* have been observed to tolerate temperatures from about 5° C. to about 40° C. and to be suitable for USDA Hardiness Zones 10 to 13.

It is claimed:

1. A new and distinct New Guinea *Impatiens* plant named 'Kiyonita' as illustrated and described.

* * * * *